United States Patent [19]

Bauer et al.

[11] 4,254,026
[45] Mar. 3, 1981

[54] WATER-SOLUBLE MONOAZO DYESTUFFS

[75] Inventors: Wolfgang Bauer, Maintal; Joachim Ribka, Offenbach am Main-Bürgel, both of Fed. Rep. of Germany

[73] Assignee: Cassella Aktiengesellschaft, Frankfurt, Fed. Rep. of Germany

[21] Appl. No.: 21,465

[22] Filed: Mar. 19, 1979

[30] Foreign Application Priority Data

May 16, 1978 [DE] Fed. Rep. of Germany ....... 2821350

[51] Int. Cl.$^3$ ............................................. C09B 29/22
[52] U.S. Cl. .................................................... 260/158
[58] Field of Search ......................................... 260/158

[56] References Cited
U.S. PATENT DOCUMENTS

| | | | |
|---|---|---|---|
| 1,833,269 | 11/1931 | Stusser | 260/158 |
| 2,283,823 | 5/1942 | Sieglitz | 260/158 |
| 3,274,171 | 9/1966 | Anderson | 260/158 |
| 4,001,206 | 1/1977 | Schoefberger | 260/158 |

FOREIGN PATENT DOCUMENTS 52-8333  3/1977  Japan .

Primary Examiner—John F. Niebling
Attorney, Agent, or Firm—Connolly and Hutz

[57] ABSTRACT

A water-soluble monoazo dyestuff useful for dyeing or printing natural or synthetic material containing hydroxyls and nitrogen has the formula

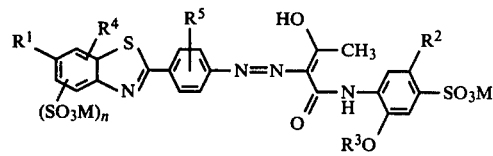

or a tautomeric form thereof, wherein $R^1$ is methyl, ethyl or 6-methyl-7-sulphobenzthiazol-2-yl, $R^2$ is methyl, methoxy or ethoxy, $R^3$ is methyl or ethyl, $R^4$ and $R^5$ may be the same or different and are hydrogen, methyl or ethyl, M is hydrogen, alkali metal or ammonium and n is 0 or 1.

3 Claims, No Drawings

WATER-SOLUBLE MONOAZO DYESTUFFS

The present invention relates to water-soluble monoazo dyestuffs which, in the form of the free acid, correspond to the formula I

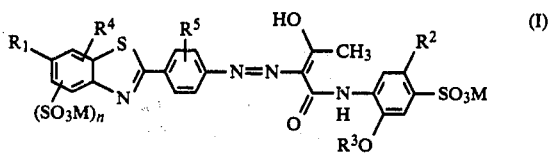

or to a tautomeric form thereof, wherein $R^1$ is methyl, ethyl, or 6-methyl-7-sulphobenzthiazol-2-yl, $R^2$ is methyl, methoxy, ethoxy, $R^3$ is methyl or ethyl, $R^4$ and $R^5$ may be the same or different and are hydrogen, methyl or ethyl, M is hydrogen, alkali metal or ammonium and n is 0 or 1, and to their manufacture and use and to the materials which have been dyed and printed therewith. Amongst the alkali metal salts, the lithium and sodium salts are preferred.

Monoazo dyestuffs of the general formula I in which $R^1$ is methyl or 6-methyl-7-sulphobenzthiazol-2-yl, $R^2$ is methyl, methoxy or ethoxy, $R^3$ is methyl or ethyl, $R^4$ and $R^5$ may be the same or different and are hydrogen or methyl, M is hydrogen, lithium, sodium or ammonium, and n is 0 or 1, are preferred within the scope of the present invention.

Monoazo dyestuffs of the formula I wherein $R^1$ is methyl or 6-methyl-7-sulphobenzthiazol-2-yl, $R^2$ is methyl, methoxy or ethoxy, $R^3$ is methyl or ethyl, $R^4$ and $R^5$ are each hydrogen, M is hydrogen, lithium, sodium or ammonium and n is 0 or 1, are particularly preferred.

The dyestuffs according to the invention, of the formula I, can be manufactured by diazotising diazo components of the formula II

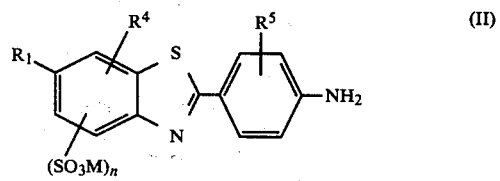

and coupling the product with coupling components of the formula III

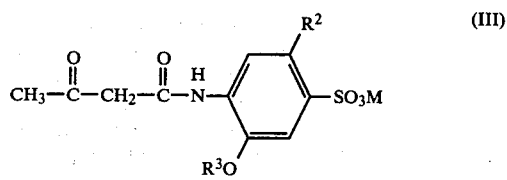

$R^1$, $R^2$, $R^3$, $R^4$, $R^5$ and M and n in the formulae II and III having the meaning mentioned above. The coupling is normally carried out within a pH range of 2 to 12, preferably 3 to 9, and at temperatures of $-10°$ C. to $+50°$ C., preferably 0° to 30° C., water being preferred as the reaction medium. If appropriate, however, monohydric or polyhydric alcohols, for example methanol, ethanol, isopropanol, n-propanol, ethylene glycol, diethylene glycol, triethylene glycol, polyethylene glycol, glycerol, pentaerythritol, mannitol, sorbitol, 1,2-polypropylene glycol, 1,3-propylene glycol, 1,3-, 2,3- and 1,4-butylene glycol, polypropylene glycol, polyvinyl alcohol, 1,6-hexylene glycol, ethylene glycol alkyl ethers, dietylene glycol alkyl ethers, triethylene glycol alkyl ethers or polyethylene glycol alkyl ethers, each of which especially having 1 to 4 C atoms in the alkyl radical, or amidic compounds, for example formamide, dimethylformamide, ε-caprolactam, pyrrolidone, N-alkylpyrrolidones having 1 to 4 C atoms in the alkyl radical, urea or thiourea, or amines, for example pyridine, ethanolamine, diethanolamine or triethanolamine, can be present in the aqueous reaction medium in order to accelerate the diazotisation and/or coupling reactions.

The monoazo dyestuffs, according to the invention, of the general formula I are excellently suitable for dyeing and printing natural or synthetic materials containing hydroxyl groups or nitrogen, especially textile fibre materials, such as cotton, regenerated cellulose, polyamide, silk or wool, and also paper, wood and leather, and as writing agents.

The dyeing and printing is carried out by the conventional processes. Brilliant yellow dyeings or prints of good evenness, which are distinguished, above all, by a surprisingly great depth of colour and fastness to light and by further good fastness properties, in particular by good fastness to washing and wet processing and also fastness to perspiration, are obtained on the textile substrates mentioned. The dyeings or prints can be discharged very readily. By virtue of their surprisingly high solubility, the monoazo dyestuffs of the invention are suitable, in particular, for semi-continuous and continuous dyeing processes, for example for the pad-jig, pad-roll, pad-steam and cold pad-batch processes. Furthermore, dyeing liquors containing the dyestuffs of the invention exhibit a low sensitivity to electrolytes. By virtue of their uniform affinity at different dyeing temperatures, the monoazo dyestuffs of the invention are also very suitable for combination shades. Because of their excellent solubility in cold water, the new monoazo dyestuffs are also suitable for dyeing unsized or sized paper in the pulp or by the dipping process. In addition to having very good fastness to water, fastness to calendering, fastness to bleeding, fastness to acid and fastness to alkali, the paper dyeings are also distinguished by resistance towards fruits juices, milk and alcoholic drinks. It is particularly advantageous that the good fastness to light and high tinctorial strength of the dyestuffs of the invention is combined with high substantivity, so that ecologically favourable dyehouse effluents are produced when dyeing cotton, regenerated cellulose, polyamide, silk, wool or leather or in paper manufacture. Compared with comparable monoazo dyestuffs which are already known in the art, such as are known, for example, from U.S. Pat. No. 3,274,171 and German application open for inspection No. 1,932,246, the monoazo dyestuffs of the invention exhibit surprising technical advantages, above all in their fastness to light, tinctorial strength, substantivity and fastness to wet processing and perspiration and in their solubility.

The good fastness to light of the dyestuffs according to the invention can, in particular, be considered surprising, because it has been known from "Ullmanns Enzyklopädie der Technischen Chemie" ("Ullmann's Encyclopaedia of Industrial Chemistry") 3rd Edition, Volume 4, (1953), page 105, that, of the thiazole derivatives, only 2-(4'-amino-3'-sulpho-phenyl)-6-methylbenzthiazole, in which a sulpho group is present in an adjacent position to the diazotisable amino group, produces dyestuffs which are fast to light. Compared with monoazo dyestuffs of this type, such as are described, for example, in German Pat. No. 293,333 and in U.S. Pat. Nos. 1,159,386 and 2,657,202, the dyestuffs of the invention exhibit not only a distinctly better tinctorial strength and substantivity, for example in polyamide and leather, but, in addition, also possess markedly better solubilites in hot and cold water.

Concentrated dyeing liquors, such as are used in semi-continuous and continuous dyeing processes do not, therefore, tend to crystallise out or to gel in the case of the dyestuffs of the invention, and in addition, they exhibit a considerably lower sensitivity to electrolytes than the comparable known dyestuffs.

A further technical advantage consists in the fact that 2-(4'-aminophenyl)-6-methylbenzthiazole-7-sulphonic acid, which is more easily accessible on an industrial scale and is more attractively priced, can be employed in the manufacture of yellow dyestuffs which are fast to light instead of 2-(4'-aminophenyl)-6-methylbenzthiazole-3',7-disulphonic acid, which can only be manufactured by a multi-stage process.

Furthermore, the dyestuffs of the present invention have better fastness to washing and perspiration, for example on cotton or polyamide.

The monoazo dyestuffs of the invention can be employed in the form of powder or granules, but also, by virtue of their excellent solubility in water, also in the form of concentrated aqueous solutions, for dyeing the said textile or non-textile, natural or synthetic fibre materials. The concentrated aqueous solutions normally contain 10 to 30% by weight, preferably 10 to 20% by weight, of pure dyestuff.

Hydrotropic compounds which are in themselves known, for example from the range of hydrotropic salts such as sodium benzoate, sodium benzenesulphonate, sodium p-toluenesulphonate, sodium xylenesulphonate or sodium N-benzyl sulphanilate, or amidic compounds containing carbonyl groups, for example formamide, dimethylformamide, acetamide, ε-caprolactam, N-methylpyrrolidone, urea, or thiourea, or alcohols, for example ethanol, n-propanol, isopropanol, ethylene glycol, diethylene glycol, triethylene glycol, polyethylene glycol, polypropylene glycol, 1,2-propylene glycol, 1,3-propylene glycol, 1,3-butylene glycol, 2,3-butylene glycol, 1,4-butylene glycol, 2,2-diethyl-1,3-propanediol, 1,6-hexylene glycol, 3-methyl-1,6-hexylene glycol and 2-methyl-1,6-hexylene glycol, 2-methyl-2,4-pentanediol, 2-ethyl-1,3-hexanediol, 2,2-dimethyl-1,3-hexanediol, diethylene glycol alkyl ethers, ethylene glycol alkyl ethers, triethylene glycol alkyl ethers or polyethylene glycol alkyl ethers, each of which especially having 1 to 4 C atoms in the alkyl radical, or amines, such as pyridine, monoethanolamine, diethanolamine or triethanolamine, are employed in order to formulate concentrated solutions which are stable on storage. Hydrotropic compounds are described, for example, in H. Rath and S. Müller, Melliand Textilberichte 40 (1959), 787 or in E. H. Daruwalla and K. Venkataraman; "The Chemistry of Synthetic Dyes", Volume VII, pages 86 to 92 (1974) and in the literature quoted in these texts. Preferred hydrotropic agents which are suitable for formulating concentrated solutions which are stable on storage, of the dyestuffs of the present invention are amidic compounds, especially urea and/or ε-caprolactam and polyhydric alcohols, in particular alkylene glycols having 2 to 6 C atoms in the alkylene chain or mixtures of these compounds. The concentrated solutions which are stable on storage normally contain 5 to 40% by weight preferably 10 to 30% by weight, of one or more hydrotropic compounds.

Auxiliaries which are in themselves known, such as, for example, surface-active agents, which are suitable for improving the wettability and/or the solubility of direct dyestuffs, can be present in the concentrated solutions or in the powder or granule forms of the dyestuffs according to the invention. Suitable surface-active agents are anionic surface-active agents, amphoteric surface-active agents or nonionic surface-active agents, such as are described, for example, in (a) Ullmanns Enzyklopädie der technischen Chemie ("Ullmann's Encyclopaedia of Industrial Chemistry"), 3rd Edition, Volume 16 (1965) pages 724 to 748;(b)"Surface Activity", 2nd Edition, chapters 10 to 15, by J. L. Moillet, B. Collie and W. Black, and (c) E. H. Daruwalla in K. Venkataraman's "The Chemistry of Synthetic Dyes", Volume VII (1974) pages 86 to 92.

It is not absolutely necessary to isolate the dyestuff press cakes or dyestuff powders and subsequently to dissolve them in water when preparing concentrated aqueous solutions, stable on storage, of the dyestuffs of the present invention. It is also possible to obtain concentrated aqueous solutions by first diazotising one or more diazo components of the formula II and then combining the product with one or more coupling components of the formula III or by reacting, with alkali metal nitrite, an aqueous mixture of a diazo component of the formula II and a coupling component of the formula III. It is also possible to employ a mixture of diazo components and/or a mixture of coupling components in this reaction. The diazo component, the coupling component and the alkali metal nitrite are employed in this reaction approximately in a molar ratio of 1:1:1. It is not necessary to add an additional acid, but it is appropriate to add ice for cooling. The reaction temperatures are normally 0° to 30° C., preferably 15° to 25° C.

Hydrotropic compounds and/or surface-active agents which are in themselves known, for example those of the type already mentioned, must be added in these processes during the diazotisation and/or coupling reactions or after coupling has been effected. Hydrotropic agents which are preferred for the preparation of concentrated solutions by these processes belong to the range of amidic hydrotropic agents, in particular urea and/or ε-caprolactam, and of polyhydric alcohols, in particular alkylene glycols having 2 to 6 C atoms in the alkylene radical, or mixtures of these compounds. Concentrated aqueous dyestuff solutions which are stable on storage and which contain about 10 to 30% by weight, preferably 10 to 20% by weight, of pure dyestuff and 5 to 40% by weight, preferably 10 to 30% by weight, of one or more hydrotropic compounds, can also be obtained by the last-mentioned processes.

The following are examples of diazo components which can be employed for the preparation of the monoazo dyestuffs according to the invention: 2-(4'-aminophenyl)-6-methylbenzthiazole (dehydrothiotoluidine), 2-(4'-aminophenyl)-6-methyl-benzthiazole-7-sulphonic acid (dehydrothiotoluidinemonosulphonic acid), 2-(4'-aminophenyl)-6-methyl-benzthiazole-5-sulphonic acid, 2-(4'-aminophenyl)-6-(6''-methylbenzthiazol-2''-yl)-benzthiazole-7''-monosulphonic acid (primulinic acid), 2-(3'-methyl-4'-amino-phenyl)-4,6-dimethylbenz-thiazole (dehydrothio-m-xylidine), 2-(3'-methyl-4'-aminophenyl)-4,6-dimethylbenzthiazole-7-sulphonic acid (dehydrothio-m-xylidinemonosulphonic acid) or mixtures of these diazo components.

The following are examples of coupling components which can be employed for the preparation of the monoazo dyestuffs, according to the invention, of the formula I: 1-acetoacetyl-amino-2-methoxy-5-methyl-benzene-4-sulphonic acid, 1-acetoacetyl-amino-2-ethoxy-5-methylbenzene-4-sulphonic acid, 1-acetoacetyl-amino-2,5-dimethoxybenzene-4-sulphonic acid, 1-acetoacetylamino-2,5-diethoxybenzene-4-sulphonic acid or mixtures of these coupling components.

In the examples which follow, parts denote parts by weight, percentages denote percentages by weight and the temperatures are quoted in degrees centigrade.

EXAMPLE 1

32 parts of 2-(4'-aminophenyl)-6-methylbenzthiazole-7-sulphonic acid (dehydrothiotoluidinemonosulphonic acid) are introduced into 200 parts of water and dissolved to form a neutral solution by means of a solution of 40 parts of sodium hydroxide in 100 parts of water and a solution of 7.59 parts of sodium nitrite in 20 parts of water is added. The resulting mixture is then run slowly into a well stirred mixture of 26 parts of 32% strength aqueous hydrochloric acid, 200 parts of ice and 100 parts of water. Stirring is continued for approx. 1 hour at 0° to 10° C. and excess nitrous acid is then removed with amidosulphonic acid. The suspension of the diazo compound is then run into a mixture of 33.4 parts of ammonium 1-acetoacetylamino-2-methoxy-5-methyl-benzene-4-sulphonate, 15.6 parts of sodium bicarbonate, 100 parts of ice and 100 parts of water. Stirring is continued for several hours at pH 6 to 7 in order to complete the coupling reaction and the dyestuff of the formula

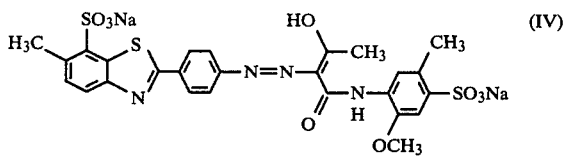

(IV)

is isolated by adding sodium chloride. This gives 200 parts of an approx. 33% strength yellow dyestuff paste, which, after drying (drying in a cabinet or spray drying) gives 90 parts of a 72% strength yellow powder (96% of theory), which has a high solubility in water.

EXAMPLE 2

45.3 parts of 2-(4'-aminophenyl)-6-(6''-methylbenz-thiazol-2''-yl)-benzthiazole-7''-monosulphonic acid (primulinic acid) are diazotised in accordance with the instructions of Example 1 and coupled with 33.4 parts of ammonium 1-acetoacetylamino-2-methoxy-5-methyl-benzene-4-sulphonate at pH 6 to 7.

The dyestuff of the structure

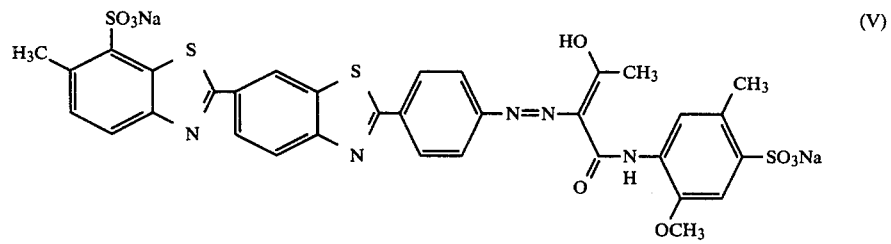

(V)

which is precipitated with the aid of sodium chloride, is filtered off. This gives 260 g of an approx. 40% strength dyestuff press cake which, after drying in a cabinet or spray drying, gives 105 g (90% of the theoretical yield) of a yellow powder with high solubility in water.

EXAMPLE 3

32 parts of 2-(4'-aminophenyl)-6-methylbenzthiazole-7-sulphonic acid (dehydrothiotoluidinemonosulphonic acid) and 33.4 parts of ammonium 1-acetoacetylamino-2-methoxy-5-methylbenzene-4-sulphonate are introduced into a mixture of 100 parts of ε-caprolactam and 160 parts of water and a solution of 7.1 parts of sodium nitrite in 10 parts of water and approx. 30 parts of ice are added. The mixture is stirred for approx. 2 hours at a temperature of 15° to 25° C. a pH of 3.5 to 4.5 being set up, and approx. 380 parts of an approx. 17% strength solution, which is stable on storage and ready for dyeing, of the dyestuff of the formula

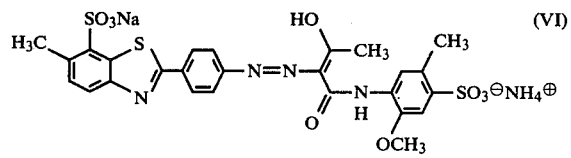

(VI)

are obtained.

EXAMPLE 4

A solution of 7.1 parts of sodium nitrite in 10 parts of water is added to a well stirred mixture of 45.4 parts of 2-(4'-aminophenyl)-6-(6''-methylbenzthiazol-2''-yl)-benzthiazole-7''-sulphonic acid (primulinic acid), 33.4 parts of ammonium 1-acetoacetylamino-2-methoxy-5-methylbenzene-4-sulphonate and 100 parts of ethylene glycol in 170 parts of water, while simultaneously adding approx. 40 parts of ice. The mixture is stirred for 2 to 3 hours at 15° to 25° C., a pH value of 3.5 to 4.5 being set up, and, after clarification by filtration, approx. 400 parts of an approx. 18% strength solution, ready for dyeing, of dyestuff of the formula

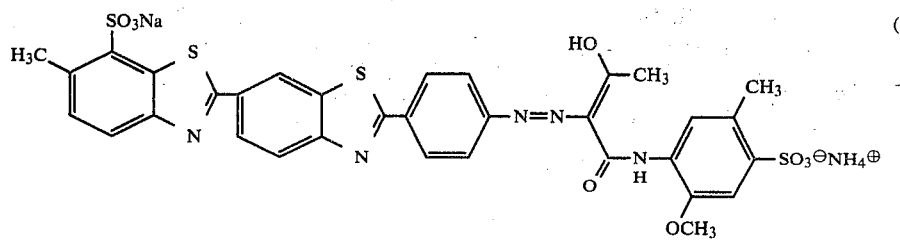

are obtained.

EXAMPLE 5

If the instructions of Example 4 are followed, using 100 parts of ε-caprolactam instead of 100 parts of ethylene glycol, approx. 400 parts of an approx. 18% strength solution, ready for dyeing, of the dyestuff of the formula VII are also obtained.

EXAMPLE 6

30 parts of the dyestuff paste obtained in accordance with Example 1 are introduced into a solution of 30 parts of urea in 40 parts of water and are dissolved at 30° to 50° C. This gives a solution, which is stable on storage, of the monoazo dyestuff of the formula IV.

EXAMPLE 7

If the instructions of Example 6 are followed, but 30 parts of ε-caprolactam are employed instead of 30 parts of urea, a true solution, which is stable on storage, of the monoazo dyestuff of the formula IV is also obtained.

EXAMPLE 8

30 parts of the dyestuff paste obtained in accordance with Example 1 are stirred into a solution of 30 parts of ethylene glycol in 40 parts of water and are dissolved at approx. 50° C. The resulting solution, which is ready for dyeing, of the dyestuff of the formula IV is stable on storage.

EXAMPLE 9

26 parts of the dyestuff press cake obtained in accordance with Example 2 are stirred into a solution of 30 parts of urea in 40 parts of water and are dissolved at approx. 50° C. A solution, which is ready for dyeing and stable on storage, of the dyestuff of the formula V is obtained.

EXAMPLE 10

A solution of 4 parts of sodium sulphate decahydrate in 200 parts of water is prepared at 40° C. in a dye beaker, located in a bath which can be heated. 0.1 part of the dyestuff powder obtained in accordance with Example 1 is added and 10 g of cotton fabric are kept in constant agitation in the ready-to-use dyeing liquor. The temperature of the dyebath is raised to 90° C. and dyeing is continued for 45 minutes at this temperature. The dyed cotton fabric is then taken out of the residual liquor, which is only slightly coloured, and residual liquor adhering to it is removed by wringing out. The dyed material is then rinsed with cold water and dried at 60° C. This gives a greenish-tinged yellow, brilliant dyeing with a great depth of colour and very good evenness, which has very good fastness properties, in particular considerable fastness to light, good fastness to washing and perspiration and fastness to alkalis, acids and formaldehyde, good dischargeability and exhibits little change in colour shade when subjected to the resin finishing which is customary for direct dyestuffs.

EXAMPLE 11

If 10 g of cotton fabric are dyed in accordance with the instructions of Example 10 using 0.1 part of the dyestuff of the formula V obtained in accordance with Example 2, a reddish-tinged yellow dyeing with good evenness and great depth of colour is obtained, which, in addition to good fastness to light, is distinguished by good fastness to washing, perspiration, acids, alkalis and formaldehyde and by exhibiting little change in colour shade when subjected to resin finishing.

EXAMPLE 12

0.15 part of the dyestuff powder obtained in accordance with Example 1 and 2 parts of 10% strength aqueous ammonium acetate solution are made up to 250 parts with water in a dye beaker and are warmed to 40° C. in a dyeing machine. 10 g of polyamide yarn are kept in constant agitation in this dyeing liquor, dyeing being carried out for 10 minutes at 40° C. and the dyeing temperature then being raised to 90° C. in the course of 30 minutes. Dyeing is continued for 90 minutes at 90° C., 1 ml of a 3% strength aqueous solution of acetic acid being added every 30 minutes. The dyed yarn is then rinsed with cold water and dried. This gives a brilliant, greenish-tinged yellow dyeing with good evenness and great depth of colour, which has considerable fastness to light and good fastness to washing and perspiration.

EXAMPLE 13

50 parts of 100% bleached sulphite cellulose are beaten in 1000 parts of water. 0.5 part of the concentrated dyestuff solution obtained in accordance with Example 3 are added to the finely distributed sulphite cellulose pulp and mixing is continued for approx. 15 minutes. The paper pulp can be sized. Paper manufacture is then carried out. A brilliant, greenish-tinged yellow dyeing with great depth of colour and good fastness properties, in particular good fastness to light, good fastness to bleeding, good fastness to acids and alkalis and good fastness to water and alcohol, is obtained on unsized or sized papers.

The effluent produced in dyeing the paper pulp is ecologically favourable.

The structural composition of further monoazo dyestuffs which can be prepared in accordance with Examples 1 to 5, can be seen from the following table.

The table indicates:

in colum 1, the diazo component of the formula II used, in column 2, the coupling component of the formula III used, and in column 3, the colour shade of the monoazo dyestuffs according to the invention on cotton.

| Examples | Diazo component of the formula (II) | Coupling component of the formula (III) | Colour shade on cotton |
|---|---|---|---|
| 14 | 2-(4'-Aminophenyl)-6-methylbenzthiazole (dehydrothiotoluidine) | 1-Acetoacetylamino-2-methoxy-5-methylbenzene-4-sulphonic acid | yellow |
| 15 | 2-(3'-Methyl-4'-aminophenyl)-4,6-dimethyl-benzthiazole-7-sulphonic acid (dehydrothio-m-xylidinemonosulphonic acid) | 1-Acetoacetylamino-2-methoxy-5-methylbenzene-4-sulphonic acid | yellow |
| 16 | 2-(4'-Aminophenyl)-6-methylbenzthiazole-7-sulphonic acid (dehydrothiotoluidinemonosulphonic acid) | 1-Acetoacetylamino-2-ethoxy-5-methyl-benzene-4-sulphonic acid | yellow |
| 17 | 2-(4'-Aminophenyl)-6-methylbenzthiazole-7-sulphonic acid (dehydrothiotoluidinemonosulphonic acid) | 1-Acetoacetylamino-2,5-dimethoxy-benzene-4-sulphonic acid | yellow |
| 18 | 2-(4'-Aminophenyl)-6-methylbenzthiazole-7-sulphonic acid | 1-Acetoacetylamino-2,5-diethoxy-benzene-4-sulphonic acid | yellow |
| 19 | 2-(4'-Aminophenyl)-6-methylbenzthiazole-7-sulphonic acid/2-(4'-aminophenyl)-6-(6''-methylbenzthiazol-2''-yl)-benzthiazole-7''sulphonic acid (primulinic acid) molar ratio 1:1 | 1-Acetoacetylamino-2-methoxy-5-methylbenzene-4-sulphonic acid | yellow |
| 20 | Primulinic acid | 1-Acetoacetylamino-2,5-dimethoxy-benzene-4-sulphonic acid | yellow |
| 21 | 2-(4'-Aminophenyl)-6-methylbenzthiazole-7-sulphonic acid | 1-Acetoacetylamino-2-methoxy-5-methylbenzene-4-sulphonic acid/ 1-acetoacetylamino-2,5-dimethoxy-benzene-4-sulphonic acid (molar ratio 1:1) | yellow |

We claim:

1. A water-soluble monoazo dyestuff of the formula

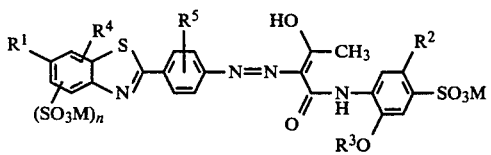

or a tautomeric form thereof, wherein $R^1$ is methyl, ethyl or 6-methyl-7-sulphobenzthiazol-2-yl, $R^2$ is methyl, methoxy or ethoxy, $R^3$ is methyl or ethyl, $R^4$ and $R^5$ may be the same or different and are hydrogen, methyl or ethyl, M is hydrogen, alkali metal or ammonium and n is 0 or 1.

2. A monoazo dyestuff according to claim 1, wherein $R^1$ is methyl or 6-methyl-7-sulphobenzthiazol-2-yl, $R^2$ is methyl, methoxy or ethoxy, $R^3$ is methyl or ethyl, $R^4$ and $R^5$ may be the same or different and are hydrogen or methyl, M is hydrogen, lithium, sodium or ammonium, and n is 0 to 1.

3. A monoazo dyestuff according to claim 1 wherein $R^1$ is methyl or 6-methyl-7-sulphobenzthiazol-2-yl, $R^2$ is methyl, methoxy or ethoxy, $R^3$ is methyl or ethyl, $R^4$ and $R^5$ are each hydrogen, M is hydrogen, lithium, sodium or ammonium and n is 0 or 1.